(12) United States Patent
Baykal

(10) Patent No.: US 9,849,234 B2
(45) Date of Patent: *Dec. 26, 2017

(54) PHYSIOLOGICAL MONITORING-BASED IMPLANTABLE DRUG INFUSION SYSTEM

(71) Applicant: Medical Software, LLC, Duluth, GA (US)

(72) Inventor: Demir Baykal, Duluth, GA (US)

(73) Assignee: Medical Software, LLC, Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,129

(22) Filed: May 15, 2017

(65) Prior Publication Data

US 2017/0246385 A1  Aug. 31, 2017

Related U.S. Application Data

(63) Continuation of application No. 14/262,104, filed on Apr. 25, 2014, now Pat. No. 9,649,438.

(51) Int. Cl.
*A61M 25/00* (2006.01)
*A61M 5/142* (2006.01)
*A61M 5/172* (2006.01)

(52) U.S. Cl.
CPC ...... *A61M 5/14276* (2013.01); *A61M 5/1723* (2013.01); *A61M 2005/1726* (2013.01); *A61M 2205/3523* (2013.01); *A61M 2230/04* (2013.01); *A61M 2230/30* (2013.01)

(58) Field of Classification Search
CPC ........ A61M 2005/1726; A61M 5/1723; A61M 2205/3523; A61M 2230/04; A61M 2230/30; A61M 5/14276
See application file for complete search history.

(56) References Cited

U.S. PATENT DOCUMENTS

| 6,635,049 B1 | 10/2003 | Robinson |
| 2007/0150019 A1 | 6/2007 | Youker et al. |
| 2013/0165918 A1 | 6/2013 | Riff |
| 2013/0310887 A1 | 11/2013 | Curtis |

OTHER PUBLICATIONS

Lee, et al., Biopotential Electrode Sensors in ECG/EEG/EMG Systems, Analog Devices, 2008, www.analog.com/MedicalICs.
Karatzis, et al., Myocardial Performance Index (Tei Index): Evaluating its Application to Myocardial Infarction, Hellenic Journal of Cardiology, 2009.

(Continued)

*Primary Examiner* — Rebecca E Eisenberg
(74) *Attorney, Agent, or Firm* — Morris, Manning & Martin, LLP; Daniel E. Sineway, Esq.

(57) ABSTRACT

A system and method for physiological monitoring and regulation of a drug infusion device. The system includes an internal compact unit that is implantable in a patient having a pulmonary disorder, the internal unit encasing a power supply, a fluid reservoir, a motor pump, a digital control unit, and a radio frequency transmitter. An infusion catheter is connected to the fluid reservoir and motor pump for automatically infusing a drug into a right ventricle of the patient during a diastole phase of a cardiac cycle. The system includes an external unit for monitoring and storing a plurality of physiological parameters of the patient and for making adjustments to a drug infusion rate.

25 Claims, 3 Drawing Sheets

(56) References Cited

OTHER PUBLICATIONS

Chaimanonart, et al., A Wireless Batteryless In Vivo EKG and Body Temperature Sensing Microsystem with Adaptive RF Powering for Genetically Engineered Mice Monitoring, Transducers 2009, Denver, CO USA, Jun. 21-25, 2009.
Ng, Jason WP, et al., Ubiquitous Monitoring Environment for Wearable and Implantable Sensors (UbiMon), International Conference on Ubiquitous Computing (Ubicomp) 2004.
Van Laerhoven, Kristof, et al., Medial Healthcare Monitoring with Wearable and Implantable Sensors, Proc. of the 3rd International Workshop on Ubiquitous Computing for Healthcare Applications, 2004.
ECG Primer: ECG Calculations, Kansas City University of Medicine and Biosciences, http://courses.kcumb.edu/physio/ecg%20primer/normecgcalcs.htm, Aug. 12, 2013.
Hemodynamic Monitoring, http://medical-dictionary.thefreedictionary.com/hemodynamic+monitoring, Jul. 31, 2013.
RV MPI, Canadian Society of Echocardiography, http://www.csecho.ca/cardiomath/?egnHD=echo&egnDisR=mpiteirv, Jul. 26, 2013.
Pulmonary Arterial Hypertension, American Lung Association, www.lung.org/lung-disease/pulmonary-arterial-hypertension/?print=t, Jul. 26, 2013.
Symptoms, Diagnosis and Treatments, American Lung Association, http://www.lung.org/lung-disease/pulmonary-arterial-hypertension/symptoms-diagnosis.html, Jul. 26, 2013.
Understanding PAH, American Lung Association, http://www.lung.org/lung-disease/pulmonary-arterial-hypertension/understanding-pah. html, Jul. 26, 2013.
What is an Electrocardiogram (EKG or ECG) Test?, WebMD, http://www.webmd.com/heart-disease/electrocardiogram?print=true, Jul. 29, 2013.
Vasodilation, Wikipedia, https://en.wikipedia.org/wikiNasodilation, Jul. 29, 2013.
Frequency-Shift Keying, Wikipedia, https://en.wikipedia.org/wiki/Frequency-shift_keying, Jul. 29, 2013.
Peristaltic Pump, Wikipedia, http://en.wikipedia.org/wiki/Peristaltic_pump, Jul. 31, 2013.
Heart chamber, Wikipedia, http://en.wikipedia.org/wiki/Heart_chamber, Jul. 31, 2013.

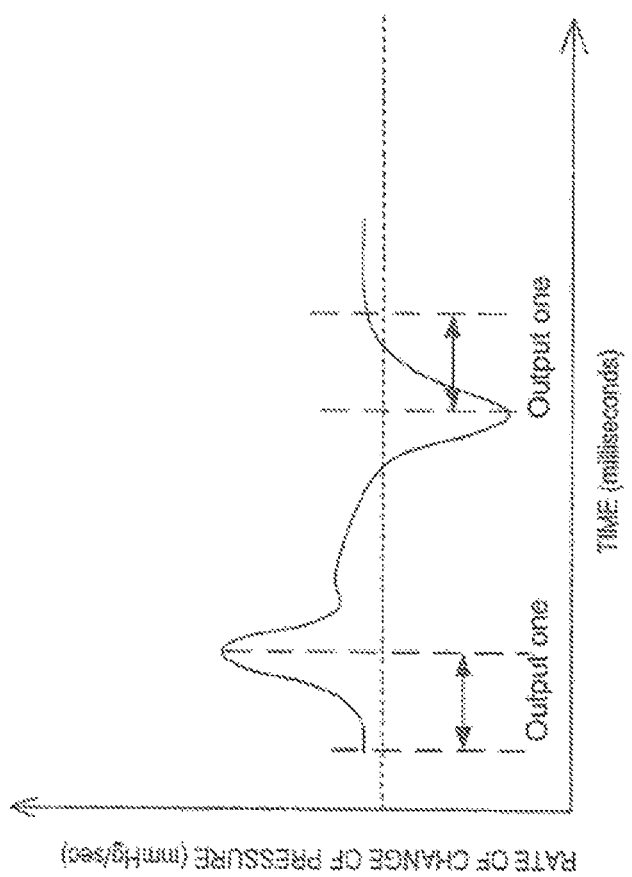

PHYSIOLOGICAL MONITORING-BASED IMPLANTABLE DRUG INFUSION SYSTEM

CLAIM OF PRIORITY

This application is a continuation of U.S. application Ser. No. 14/262,104, filed Apr. 25, 2014, and entitled "Physiological Monitoring-Based Implantable Drug Infusion System", which is incorporated herein by reference in its entirety.

TECHNICAL FIELD

Embodiments of the invention generally relate to medical devices and, more specifically, to implantable drug infusion systems associated with physiological monitoring systems.

BACKGROUND

In the field of medical science, pulmonary arterial hypertension (PAH) is a heart/lung disorder in which the blood pressure in the pulmonary arteries and/or pulmonary arterioles far exceeds normal levels. The precise causes of PAH are still not completely known. PAH manifests in the form of shortness of breath, dizziness, fainting, and other symptoms, all of which are exacerbated by physical exertion and stress. Pulmonary hypertension can be a severe disease with a markedly decreased exercise tolerance and can result in heart failure, and eventually death, for some patients.

The electrocardiogram (ECG or EKG) complex is defined by a plurality of waves, segments, and intervals as follows. The P-wave is the first component of the ECG complex and corresponds to atrial depolarization (contraction). It is usually a positive deflection from the baseline. The QRS complex corresponds with ventricular depolarization (contraction) and is measured from the beginning of the Q-wave or R-wave (if no Q-wave is present) to the end of the S-wave. The normal duration of the QRS complex is 0.04-0.11 seconds. The Q-wave is the first negative deflection of the QRS complex. The R-wave is the first positive deflection of the complex. The S-wave is the negative deflection following the R-wave. Not every QRS complex has a Q, R, and S-wave. The T-wave corresponds with ventricular repolarization (relaxation). The U-wave is a small wave of low voltage and, if present, follows the T-wave. The PR segment begins at the end of the P-wave and continue until the beginning of the QRS complex. The PR interval includes the P-wave and PR segment. The normal PR interval measurement is 0.12-0.20 seconds. The ST segment is measured from the end of the QRS complex to the beginning of the T-wave. The QT interval corresponds with ventricular depolarization (contraction) and repolarization (relaxation). The normal QT interval measurement is 0.32-0.40 seconds.

SUMMARY

The disclosed embodiments relate to medical devices corresponding to physiologically or pathophysiologically regulated or regulatable drug infusion. According to one embodiment, the disclosure pertains to medical devices and methods associated with intrapulmonary arterial drug delivery to patients suffering from pulmonary arterial hypertension, wherein the disclosed device is based on an implantable drug infusion assembly that has the ability to deliver drugs by physiological, automatic or external means, and yet does not compromise the health safety issues of pulmonary patients who receive such drug dosages.

In one embodiment, a system is provided for physiological monitoring and regulation of a drug infusion device. The system includes an internal compact unit that is implantable in a patient having a pulmonary disorder, the internal unit encasing a power supply, a fluid reservoir, a motor pump, a digital control unit, and a radio frequency transmitter. An infusion catheter is connected to the fluid reservoir and motor pump for automatically infusing a drug into a right ventricle of the patient during a diastole phase of a cardiac cycle. The system includes an external unit for monitoring and storing a plurality of physiological parameters of the patient and for making adjustments to a drug infusion rate.

In one embodiment, an infusion catheter is provided for delivery of a drug into a patient having a pulmonary disorder. The infusion catheter includes a radially dense helical structure made of a polyurethane material and having a supporting steel frame. A hemodynamic pressure sensor is mounted on a tip of the catheter for measuring a relative change in hemodynamic pressure over time. A biopotential sensor including a biopotential sensing electrode is mounted on a tip of the catheter for sensing an electrocardiogram signal of the patient. The infusion catheter is connected by a valve to a fluid reservoir and a motor pump in an implantable device and automatically infuses a drug into a right ventricle of the patient during a diastole (relaxation) phase of a cardiac cycle at a rate dependent on the measured change in hemodynamic pressure.

In one embodiment, a method is provided for hemodynamic monitoring of a patient diagnosed with pulmonary hypertension and infusion of a therapeutic drug by an implantable drug infusion device. The method includes monitoring the relative change in hemodynamic pressure in a patient's right ventricle over time by a pressure sensor mounted on a tip of an infusion catheter in the implantable device; sensing an electrocardiogram signal of the patient by a biopotential sensor including a biopotential sensing electrode mounted on a tip of the infusion catheter; and infusing the therapeutic drug into the right ventricle during a diastole phase of a cardiac cycle at a rate dependent on the monitored relative change in hemodynamic pressure. The drug is pumped from a fluid reservoir in the implantable device through the infusion catheter into the patient's right ventricle through an infusion port.

BRIEF DESCRIPTION OF THE DRAWINGS

These and other advantages and aspects of the embodiments of the disclosure will become apparent and more readily appreciated from the following detailed description of the embodiments taken in conjunction with the accompanying drawings, as follows.

FIG. 3 illustrates and exemplary schematic representation of rate of pressure change in the right ventricle.

DETAILED DESCRIPTION

The following detailed description is provided as an enabling teaching of embodiments of the invention. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances. Thus, the following description is provided as illustrative of the principles of the invention and not in limitation thereof, since the scope of the invention is defined by the claims.

According to one embodiment, the implantable drug infusion system provides pulmonary arterial delivery of drugs to patients with pulmonary arterial hypertension. Infusion systems have been used in drug delivery prior to the present disclosure. However, prior systems have not provided the capability of delivering drugs based on sensing and analyzing cyclic hemodynamic, electrical occurrences within the heart. The infusate may be a vasodilatory agent or may serve the purpose of delivering gene therapy.

In one embodiment, the design of the drug infusion catheter includes a unique design to ensure forward-only phasic flow, thereby minimizing the risk of catheter malfunction, and therefore providing maximum patient safety. Furthermore, using a drug infusion system, as described herein, for delivering drugs to pulmonary hypertension patients is also a unique concept.

Figure 1:
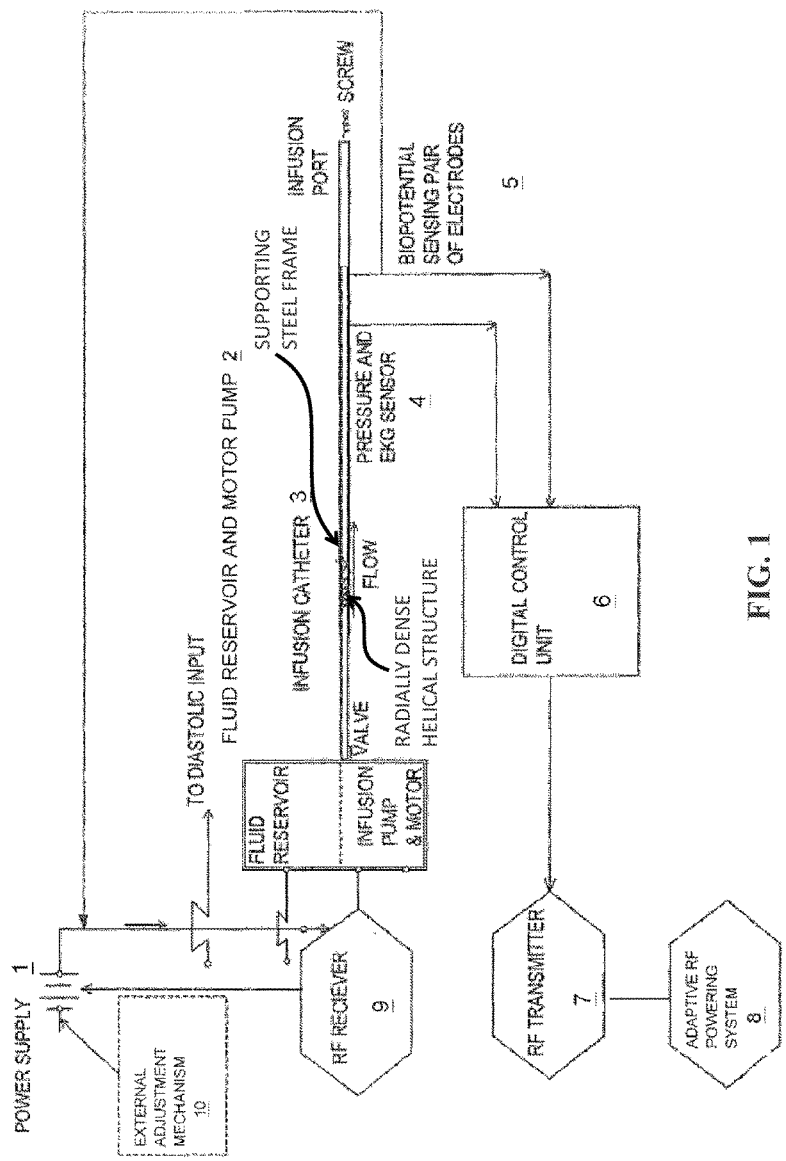
FIG. 1 illustrates and implantable drug infusion system in accordance with an exemplary embodiment.

An embodiment of the implantable drug infusion system is illustrated in FIG. 1. The disclosed system includes both an external unit and an internal unit. The internal unit resembles a pacemaker in design, and is typically implanted inside a pocket positioned under the collar bone and connected to the heart using an infusion catheter. The components of the internal unit include: power supply 1, fluid reservoir and motor pump 2, infusion catheter 3, pressure sensor 4, biopotential (ECG) sensor 5, digital control unit 6, and RF transmitter 7.

The external unit components are those components that are located outside the patient's body, and such external components are generally related to aspects of monitoring and storing of various physiological parameters and to making external adjustments to the drug flow rate. Examples of various physiological parameters include, but are not limited to, heart rate, EKG, and right ventricle pressure. In one exemplary embodiment, the components of the external unit include adaptive RF powering system 8, RF receiver 9, and an adjustment component 10.

It will be understood that the power supply 1, fluid reservoir and motor pump 2, digital control unit 6, and RF transmitter 7 of the internal unit of the implantable drug infusion system are typically encased in a separate unit herein referred to as the internal compact unit. Usually, the internal compact unit is circular or elliptical in shape, so as to avoid the presence of sharp corners that might damage internal tissues or penetrate a patient's skin. In one embodiment, dimensions of the internal compact unit of the drug infusion system are such that the volume of the internal compact unit is between 6-8 cubic centimeters. As will be understood and appreciated by one of ordinary skill in the art, standard pacemaker pulse generators are typically sized similar to, or somewhat smaller than, the internal compact unit of the disclosed drug infusion system. However, various embodiments of the drug infusion system could include different shapes and sizes as will occur to one of ordinary skill in the art, and are not limited to the specific dimensions or shapes described herein. Although in the exemplary embodiments described herein, the drug infusion system includes ten components, no limitation of the scope of the disclosure is intended thereby; any alterations and further modifications of the described or illustrated embodiments, and any further applications of the principles of the disclosure are contemplated as would normally occur to one skilled in the art to which the disclosure relates. For example, the number of components comprising the drug infusion system can involve greater than or, alternatively, fewer than ten components.

For the purpose of promoting an understanding of the principles of the disclosure, reference will now be made to the embodiments illustrated in the drawings and specific language will be used to describe the same. In other words, the various components illustrated in FIG. 1 that include the internal and external units of the drug infusion system will be described in greater detail.

Power Supply

For operation of the electrical circuitry within the internal compact unit of the disclosed implantable drug infusion system, a power supply 1 is provided. In one embodiment, the power supply may include a lithium battery (for example, using lithium magnesium dioxide, or lithium iodine, or lithium carbon monofluoride). Such lithium batteries typically have long lives, slow discharge rates, and are suitable for memory backup. As will be understood, the life of such batteries is usually estimated through monitoring of internal resistance similar to current pacemaker systems. However, since the implantable drug infusion system is expected to stay implanted inside a patient's heart for a duration shorter than that of pacemakers, complicated methods of estimation of the life of the battery are generally not required. In one embodiment, the dimensions of the power supply component of the disclosed drug infusion system are 20 millimeters×20 millimeters×2 millimeters.

Fluid Reservoir and Infusion Pump

According to one embodiment, the disclosed drug infusion system utilizes a fluid reservoir connected to an infusion pump for storage and distribution of the given drug based on the cardiac cycle of a patient's heart. As seen in FIG. 1, the fluid reservoir and infusion pump component is labeled with reference number 2. The fluid reservoir is essentially a subcutaneous reservoir that stores the drug. The fluid reservoir is filled periodically, or as needed, by making a perforation on the patient's skin using a needle. As will be understood by one of ordinary skill, the reservoir chamber that stores the drug is kept separate from the motor pump chamber which pumps the drug out from the reservoir chamber into the patient's body. The motor pump chamber 2 is connected to the power supply 1. Generally, the drug that will be administered to a patient is in constant flow from the reservoir chamber to the pump chamber 2. The rate of flow of the drug from the pump chamber 2 to the infusion catheter 3 is regulated by the output from power supply 1 to the chamber 2, as shown in FIG. 1. It will be understood that the rate of flow from the pump chamber 2 to the infusion catheter 3 ceases during systole (contraction), ensuring that the power supply operated pump creates a peristaltic flow during a mechanically less active diastolic (relaxation) phase of a cardiac cycle. In one embodiment, the rate of flow of the drug can be adjusted manually by a clinician.

Infusion Catheter

Figure 2:
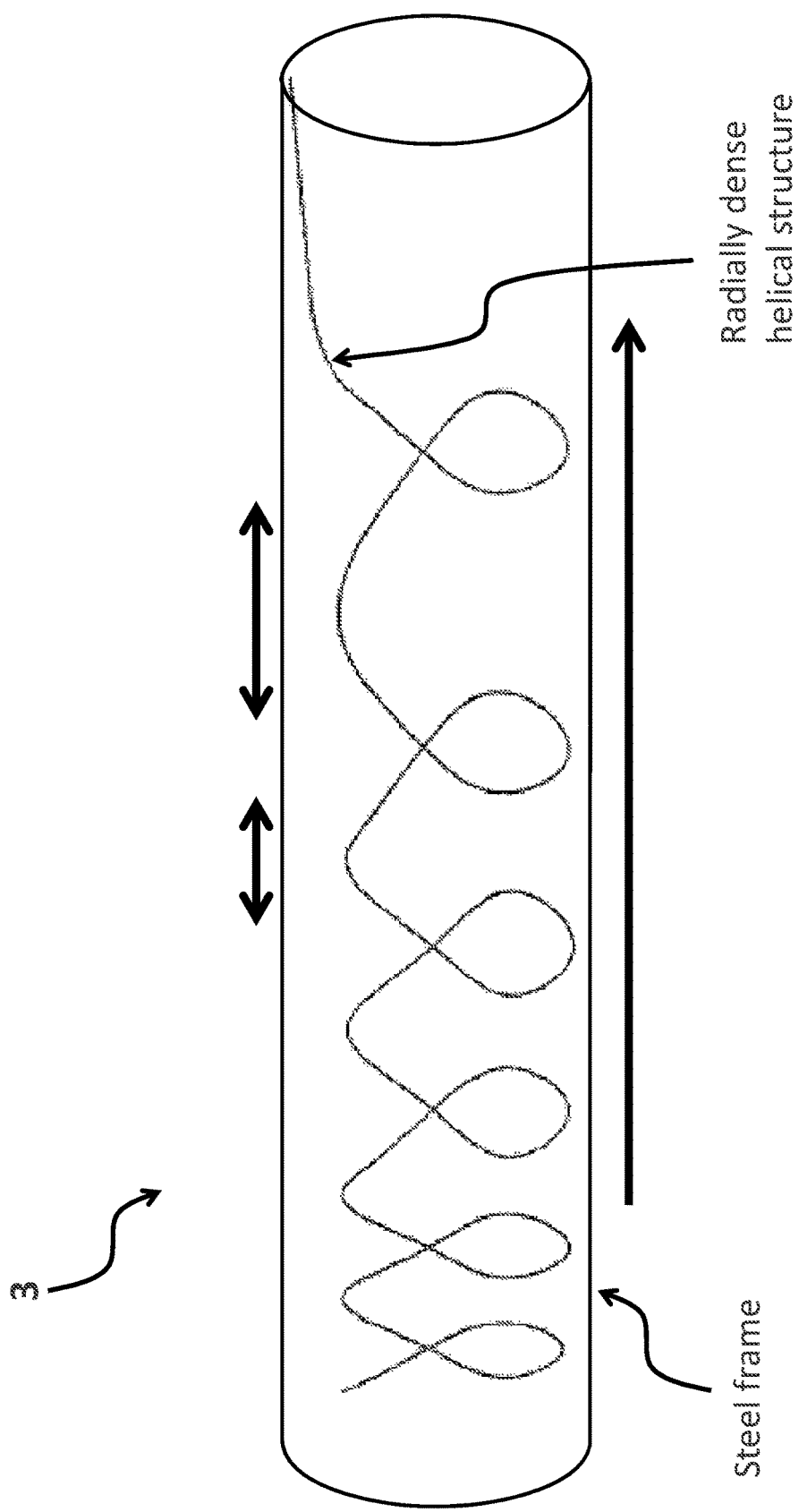
FIG. 2 illustrates a magnified view of an infusion catheter in accordance with an exemplary embodiment.

An infusion catheter 3 is connected via a valve to a fluid reservoir and motor pump 2. As will be understood by one of skill in the art, the infusion catheter 3 forms the conduit for drug delivery to the patient. A magnified view of an embodiment of the infusion catheter 3 is shown in FIG. 2. According to one aspect, the infusion catheter 3 is made of polyurethane with the supporting steel frame designed to provide radial strength and reservoir-like functionality to the proximal portion. As shown in FIG. 2, the proximal portion of the infusion catheter 3 includes a radially dense helical structure that proximally functions as a fluid reservoir when there is no peristaltic flow created by the motor pump 2 during systole. It will be understood that the helical structure is designed in such a manner that it is resistant to collapse in the proximal portion during systole when 40 min to 100 mm Hg pressure is generated. In the mid and distal portions of the catheter 3, the steel frame is more longitudinally oriented, increasingly parallel to the long axis of the catheter 3, and becomes progressively less dense. As will be understood and appreciated, the distal collapse of the catheter 3 prevents blood entrapment that could lead to clot formation. The reservoir functionality provided by the proximal part of the catheter 3 helps in flushing any residual blood within the more distal parts as peristaltic flow begins with a next cycle. From the foregoing, it will be appreciated that the novel infusion catheter 3 allows unidirectional (i.e., forward) flow of the drug only during certain phases of the patient's cardiac cycle, i.e., during diastole. The interior of the distal portions of the catheter 3 (having exemplary dimensions of about 2 cm to 3 cm, although other dimensions are possible) is coated with heparin or other thrombin inhibitors to prevent clotting.

Generally, the infusion catheter 3 contains pressure and EKG sensors 4 located at its tip, and an infusion hole 1 cm away from the tip. As shown in FIG. 1, a screw attached at the end of the infusion catheter allows the catheter to be anchored to the right ventricle wall in the patient's heart, similarly to a pacemaker.

Pressure Sensor

As seen in FIG. 1, a hemodynamic pressure sensor 4 monitors the relative change in right ventricle pressure change over time. For example, the rate of change of ventricle pressure can be expressed mathematically as dp/dt wherein dp=pressure change, dt=time interval of change. As shown in FIG. 3, a typical dp/dt (vertical axis) versus time (horizontal axis) curve contains sharp deflections very relevant to the performance of the right ventricle which is closely related to pulmonary arterial pressures. As illustrated in FIG. 3, there are two positive deflections observed in this curve.

One early positive deflection from the base of the curve to the point at which dp/dt is maximum occurs during isometric contraction of the ventricle, whereas a late upward deflection from the point at which dp/dt is minimum to the base occurs during isovolumetric relaxation. Analogous to the Tei index (myocardial performance index) or mechanical performance index determined by ultrasonography, the time duration of the sum of these two upward deflections normally should not exceed 20%-25% of the time duration of a complete cardiac cycle.

As will be appreciated, aspects of this disclosure allow the infusion rate to be adjusted automatically or manually by external procedures. For example, an algorithm (method) can be used for the automatic adjustment of the infusion rate. It will occur to one of ordinary skill that this technique of measuring relative changes in ventricle pressure has several advantages over measurement of absolute pressures.

One advantage is avoiding intrinsic difficulties, including the need for periodic calibration, associated with absolute pressure measurement. Another advantage is that the relative changes in ventricle pressure (typically measured in increments in pressure dp at dt intervals) can be converted into digital values, and expressed as an output comprising zeroes and ones. For example, positive increments in dp are expressed as an output one ('1'), as indicated in FIG. 3. On the other hand, zero or negative increments in dp are expressed as an output zero ('0'). Within one cardiac cycle, the ratio of the duration of sharp positive deflections (output one) to the time duration of a complete cardiac cycle is an indicator of right ventricular condition. Normally this ratio lies in the range 0.2-0.4. The infusion rate can be increased automatically if the ratio exceeds 0.4. The ratio of output one ('1') versus output zero ('0') is closely related to the condition of the right ventricle, and moreover, the lower this ratio, the better is the condition of the right ventricle. It will occur to one of ordinary skill that even in normal individuals, pulmonary artery pressures may elevate with exercise occasionally. Thus, it will be appreciated that it makes more sense to track right ventricle performance in a relative sense, as opposed to attempting absolute pulmonary arterial pressure measurements. Moreover, it will be known by one skilled in the art that performance of the right ventricle is more closely related to the prognosis, and thus several aspects of the disclosure present in various beneficial ways.

As shown in FIG. 1, a pressure sensor 4 is connected to a digital control unit 6 which will be further described below. In one example of the disclosed system, details of an exemplary system architecture involving pressure sensors, and various other issues relating to gathering and analyzing data collected by such sensors (including the digital control unit 6 as shown in FIG. 1) are discussed in the following technical publication: "Ubiquitous Monitoring Environment for Wearable and Implantable Sensors (UbiMon)," by Jason W. P. Ng, Benny P. L. Lo et al., which is incorporated by reference herein. Accordingly, these details are not described herein.

Biopotential (ECG Sensor) Sensing Electrodes

In one embodiment, the electrocardiogram (EKG or ECG) signal is sensed by a pair of biopotential sensing electrodes 5 (although, other sensing mechanisms may be used). The EKG sensor ensures that the power supply operates the pump motor only in diastole (relaxation). Typically, EKG signals occupy about a 100 Hz bandwidth, and have a dynamic range of amplitude varying between 20 µV-5 mV. In one aspect, these EKG signals are relayed to the power supply 1 either via a wire, as commonly done in typical pacemakers, or communicated wirelessly with the help of a digital control unit 6. Drug infusion can start 80 milliseconds after a 2.5 mV biopotential is sensed (i.e., QRS deflection) and stops with the next biopotential sensing (i.e., next QRS deflection). According to one embodiment, the sensing electrodes 5 and the associated system are based on the design proposed in the following technical publication: "A Wireless Batteryless In Vivo EKG and Body Temperature Sensing Microsystem with Adaptive RF Powering For Genetically Engineered Mice Monitoring" by Nattapon Chaimanonari and Darrin J. Young, incorporated by reference herein. The sensing electrodes 5 may include virtually any sensing mechanism as will occur to one of ordinary skill in the art.

Digital Control Unit

In one embodiment, a pair of biopotential sensing electrodes 5 is connected to a digital control unit 6. Digital control unit 6 further includes an 8 bit analog to digital (A/D) converter, a detector for sensing RF power, and a parallel to serial converter. As will be understood, EKG or hemodynamic data (dp/dt) is digitized to 8 bits. Furthermore, in one aspect, the digitization process (or, in general, the digital control unit 6) clamps a positive dp/dt value to output one ('1') if the positive dp/dt value exceeds a predetermined threshold. Similarly, the digitization process clamps a negative dp/dt value to output one ('1') if the negative dp/dt value is less than a predetermined threshold. Alternately, a positive dp/dt value is clamped to output zero ('0') if the positive dp/dt value is less than the predetermined threshold. Similarly, a negative dp/dt value is clamped to output zero ('0') if the negative dp/dt value exceeds the predetermined threshold. The performance of a patient's heart, in such situations, is given by the ratio of output one ('1') and output zero ('0').

Subsequently, the digitized data is appended to a one bit RF power level data; the resulting data is converted into a serial data stream using a parallel to serial converter (in conjunction with a multiplexer, and finally transmitted to the RF transmitter 7. Details of a digital control unit are described in the article: "A Wireless Batteryless In Vivo EKG and Body Temperature Sensing Microsystem with Adaptive RF Powering for Genetically Engineered Mice Monitoring," by Nattapon Chaimanonari and Darrin J Young, incorporated by reference herein. Therefore, further details are not described herein. As will be appreciated, in alternate embodiments, a digital control unit includes a microprocessor, or any other combination of electrical components providing the various functionalities described above.

RF Transmitter

The physiological data comprising a patient's vital signs such as right ventricle pressure, EKG signals, etc. are sent to an RF transmitter 7, and then transmitted wirelessly from internal RF transmitter 7 to the external RF receiver 9. In one embodiment, the RF transmitter 7 can be a Frequent Shift Keying (FSK) transmitter. FSK is a frequency modulation scheme in which digital information is transmitted through discrete frequency changes of a carrier signal. As will be understood and appreciated, however, embodiments of the disclosed device are not limited to the specific RF transmitter described.

Adaptive RF Powering System

In one embodiment, an external adaptive RF powering system is coupled wirelessly to the digital control unit to regulate the voltage supply for the implantable device.

RF Receiver

The RF data received at the RF receiver 9 can be stored in a digital computer for future analysis and can also be used to determine infusion rate of the drug. In one embodiment, the RF receiver 9 can be a Frequent Shift Keying (FSK) receiver. As will be understood and appreciated, however, embodiments of the disclosed device are not limited to the specific RF receiver described. The data received at the RF receiver 9 can be stored in a digital computer for future analysis and can also be used to determine the infusion rate of the applicable drug. As will be understood, automatic adjustment of the infusion rate is also programmable through the RF transmitter 7, RF receiver 9 and power supply 1. Initially, however, dose adjustment should be done manually and externally by the clinician reviewing stored data, although this is not technically required for operation of the disclosed device.

External Adjustment Mechanism

An external adjustment mechanism 10 allows the external unit to be of flexible design. In one embodiment, the external adjustment mechanism 10 is designed such that the entire external unit of the implantable drug infusion system could be assembled into a single handheld unit (comparable to the size of state-of-the-art smartphones of today), that can further fit inside a case or can be worn on a belt. The handheld unit can include a personal digital assistant (PDA), smartphone, tablet, or other portable computing device. Therefore, it will be understood and appreciated that the disclosed drug infusion system provides the benefits of being lightweight and portable.

The corresponding structures, materials, acts, and equivalents of all means plus function elements in any claims below are intended to include any structure, material, or acts for performing the function in combination with other claim elements as specifically claimed.

Those skilled in the art will appreciate that many modifications to the exemplary embodiments are possible without departing from the scope of the present invention. In addition, it is possible to use some of the features of the embodiments disclosed without the corresponding use of the other features. Accordingly, the foregoing description of the exemplary embodiments is provided for the purpose of illustrating the principles of the invention, and not in limitation thereof, since the scope of the invention is defined solely by the appended claims.

What is claimed:

1. A system for physiological monitoring and regulation of a drug infusion device, comprising:
   an internal compact unit that is implantable in a patient, the internal compact unit comprising a radio frequency transmitter, a fluid reservoir, and a motor pump;
   an infusion catheter comprising a radially dense helical structure and a supporting frame, wherein the infusion catheter is connected to the fluid reservoir and motor pump for infusing a drug into the patient; and
   an external unit in communication with the radio frequency transmitter that monitors one or more physiological parameters of the patient for making adjustments to a drug infusion rate.

2. The system for physiological monitoring and regulation of claim 1, wherein the infusion catheter further comprises a hemodynamic pressure sensor and a biopotential sensor.

3. The system for physiological monitoring and regulation of claim 2, wherein the hemodynamic pressure sensor is located at a tip of the infusion catheter and measures a relative change in hemodynamic pressure over time.

4. The system for physiological monitoring and regulation of claim 3, wherein the fluid reservoir comprises the drug, and wherein the drug can be delivered through the infusion catheter at the drug infusion rate, and wherein the drug infusion rate can be automatically changed in response to the hemodynamic pressure measured by the hemodynamic pressure sensor.

5. The system for physiological monitoring and regulation of claim 2, wherein the biopotential sensor comprises a sensing electrode located at a tip of the infusion catheter for sensing an electrocardiogram signal.

6. The system for physiological monitoring and regulation of claim 2, wherein the internal compact unit further comprises a digital control unit.

7. The system for physiological monitoring and regulation of claim 6, wherein the biopotential sensor and the hemodynamic pressure sensor are connected to the digital control unit which digitizes one or more physiological signals received from these sensors and sends the digitized physiological signals to the radio frequency transmitter.

8. The system for physiological monitoring and regulation of claim 7, wherein the radio frequency transmitter transmits the digitized physiological signals wirelessly to the external unit.

9. The system for physiological monitoring and regulation of claim 1, wherein the external unit further comprises an adjustment component.

10. The system for physiological monitoring and regulation of claim 9, wherein the adjustment component comprises a handheld electronic device.

11. The system for physiological monitoring and regulation of claim 9, wherein the adjustment component is configured to adjust the drug infusion rate of the internal compact unit.

12. The system for physiological monitoring and regulation of claim 1, wherein the fluid reservoir comprises a subcutaneous chamber for storing the drug to be automatically infused.

13. The system for physiological monitoring and regulation of claim 1, wherein the motor pump is connected to a power supply and pumps the drug from the fluid reservoir to the infusion catheter, and wherein the drug flow rate is regulated by an output from the power supply to the fluid reservoir.

14. The system for physiological monitoring and regulation of claim 1, wherein the internal compact device is implanted inside a pocket positioned under a collar bone of the patient.

15. The system for physiological monitoring and regulation of claim 1, wherein the infusion catheter is in contact with a heart right ventricle.

16. The system for physiological monitoring and regulation of claim 1, further comprising a pulse oximeter located at a tip of the infusion catheter and configured to measure oxygen saturation in the patient.

17. The system for physiological monitoring and regulation of claim 1, wherein the system is used for the treatment of pulmonary arterial hypertension and/or heart failure via drug infusion.

18. A system for physiological monitoring and regulation of a drug infusion device, comprising:
an internal compact unit that is implantable in a patient, the internal compact unit comprising a radio frequency transmitter, a fluid reservoir, and a motor pump;
an infusion catheter connected to the fluid reservoir and motor pump for infusing a drug into the patient, wherein the infusion catheter comprises a hemodynamic pressure sensor located at the tip of the infusion catheter that measures relative change in pressure over time; and
an external unit in communication with the radio frequency transmitter that controls adjustments to a drug infusion rate based on the relative change in pressure.

19. The system for physiological monitoring and regulation of claim 18, further comprising a biopotential sensor including a biopotential sensing electrode mounted on the tip of the infusion catheter for sensing an electro cardiogram signal of the patient.

20. The system for physiological monitoring and regulation of claim 19, wherein the internal compact unit further comprises a digital control unit.

21. The system for physiological monitoring and regulation of claim 20, wherein the biopotential sensor and the hemodynamic pressure sensor are connected to the digital control unit which digitizes a plurality of physiological signals received from these sensors and sends the digitized physiological signals to the radio frequency transmitter.

22. The system for physiological monitoring and regulation of claim 18, wherein the infusion catheter further comprises a radially dense helical structure and a supporting frame.

23. The system for physiological monitoring and regulation of claim 18, further comprising a pulse oximeter located at a tip of the infusion catheter and configured to measure oxygen saturation in the patient.

24. The system for physiological monitoring and regulation of claim 18, wherein the system is used for the treatment of pulmonary arterial hypertension and/or heart failure via drug infusion.

25. A drug infusion device for infusing a drug into a patient, comprising:
a catheter for infusing the drug into the patient, the catheter comprising a radially dense helical structure and a supporting frame;
a fluid reservoir for storing the drug; and
a pressure sensor located at the tip of the catheter that measures relative change in pressure over time,
wherein the drug is delivered to the patient through the catheter based on the relative change in pressure over time.

* * * * *